US008513216B2

(12) United States Patent
Stroumpoulis et al.

(10) Patent No.: US 8,513,216 B2
(45) Date of Patent: *Aug. 20, 2013

(54) POLYSACCHARIDE GEL FORMULATION HAVING INCREASED LONGEVITY

(75) Inventors: Dimitrios Stroumpoulis, Goleta, CA (US); Christopher S. Mudd, Goleta, CA (US); Ahmet Tezel, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 12/558,270

(22) Filed: Sep. 11, 2009

(65) Prior Publication Data
US 2010/0004198 A1 Jan. 7, 2010

Related U.S. Application Data

(63) Continuation of application No. 12/276,167, filed on Nov. 21, 2008, now Pat. No. 8,394,782.

(60) Provisional application No. 60/991,473, filed on Nov. 30, 2007.

(51) Int. Cl.
*A61K 31/70* (2006.01)

(52) U.S. Cl.
USPC .......................................................... 514/54

(58) Field of Classification Search
USPC .......................................................... 514/54
See application file for complete search history.

(56) References Cited

U.S. PATENT DOCUMENTS

| | | | |
|---|---|---|---|
| 2,128,827 A | 8/1938 | Killian | |
| 3,548,056 A | 12/1970 | Eigen et al. | |
| 3,763,009 A | 10/1973 | Suzuki | |
| 3,949,073 A | 4/1976 | Daniels et al. | |
| 4,060,081 A | 11/1977 | Yannnas et al. | |
| 4,140,537 A | 2/1979 | Luck et al. | |
| 4,233,360 A | 11/1980 | Luck et al. | |
| 4,273,705 A | 6/1981 | Kato | |
| 4,279,812 A | 7/1981 | Cioca | |
| 4,424,208 A | 1/1984 | Wallace et al. | |
| 4,501,306 A | 2/1985 | Chu et al. | |
| 4,582,640 A | 4/1986 | Smestad et al. | |
| 4,582,865 A | 4/1986 | Balazs et al. | |
| 4,605,691 A | 8/1986 | Balazs et al. | |
| 4,636,524 A | 1/1987 | Balazs | |
| 4,642,117 A | 2/1987 | Nguyen et al. | |
| 4,713,448 A | 12/1987 | Balazs | |
| 4,716,154 A | 12/1987 | Malson et al. | |
| 4,803,075 A | 2/1989 | Wallace et al. | |
| 4,886,787 A * | 12/1989 | de Belder et al. ............... | 514/57 |
| 5,009,013 A | 4/1991 | Wiklund | |
| 5,087,446 A | 2/1992 | Suzuki et al. | |
| 5,091,171 A | 2/1992 | Yu et al. | |
| 5,143,724 A | 9/1992 | Leshchiner | |
| 5,246,698 A | 9/1993 | Leschiner et al. | |
| 5,314,874 A | 5/1994 | Miyata et al. | |
| 5,328,955 A | 7/1994 | Rhee et al. | |
| 5,356,883 A | 10/1994 | Kuo et al. | |
| 5,399,351 A | 3/1995 | Leschiner et al. | |
| 5,428,024 A | 6/1995 | Chu et al. | |
| 5,531,716 A | 7/1996 | Luzio et al. | |
| 5,565,519 A | 10/1996 | Rhee et al. | |
| 5,571,503 A | 11/1996 | Mausner | |
| 5,614,587 A | 3/1997 | Rhee et al. | |
| 5,616,568 A | 4/1997 | Pouyani et al. | |
| 5,616,611 A | 4/1997 | Yamamoto | |
| 5,616,689 A | 4/1997 | Shenoy et al. | |
| 5,633,001 A | 5/1997 | Agerup | |
| 5,643,464 A | 7/1997 | Rhee et al. | |
| 5,676,964 A | 10/1997 | della Valle | |
| 5,823,671 A | 10/1998 | Mitchell et al. | |
| 5,824,333 A | 10/1998 | Scopelianos et al. | |
| 5,827,529 A | 10/1998 | Ono et al. | |
| 5,843,907 A | 12/1998 | Sakai | |
| 5,880,107 A | 3/1999 | Buenter | |
| 5,886,042 A | 3/1999 | Yu et al. | |

(Continued)

FOREIGN PATENT DOCUMENTS

| | | |
|---|---|---|
| CA | 949965 | 6/1974 |
| EP | 0273823 | 7/1988 |

(Continued)

OTHER PUBLICATIONS

Sculptra® Aesthetic Directions for Use (Jul. 2009) sanofi-aventis U.S. LLC.
Visiol Directions for Use. http://www.trbchemidica.com/index.php?option=com_content&task=view&id=25&Itemid=41 Feb. 25, 2010.
TRB Chemedica Ophthalmic Line.
Osmitrol Official FDB Information, side effects and uses. http://www.drugs.com/pro.osmitrol.html Feb. 25, 2010.
Intramed Mannitol 20% m/v Infusion. http://home.intekom.com/pharm/intramed/manit120.html Feb. 25, 2010.
J. Cataract & Refract Surg, vol. 31, Jun. 2005, pp. 1213-1218.
*Aesthetic Buyers Guide*, "Juvéderm Raises Standards" Jan./Feb. 2007 (5 pp.), www.miinews.com.
McPherson, et al., Development and Biochemical Characterization of Injectable Collagen, J. Dermatol Surg Oncol, 1988, 14 Supp 1.
Albano, Emanuele, et al., "Hyroxyethyl Radicals in Ethanol Hepatotoxicity," Frontiers in Bioscience 4:533-540 (1999).
Baumann et al. "Juvederm vs. Zyplast Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).
Beasley et al. :Hyaluronic acid fillers: a comprehensive review. Facial Plast. Surg. 25(2): 86-94 (2009).

(Continued)

*Primary Examiner* — Elli Peselev
(74) *Attorney, Agent, or Firm* — Linda Fox; Stephen Donovan; Debra Condino

(57) ABSTRACT

Described herein are polysaccharide gel formulations including at least one inhibitor of polysaccharide degradation and methods of making the same. The methods described herein involve the steps of providing at least one polysaccharide and incorporating at least one inhibitor of degradation into the polysaccharide. In some embodiments, the incorporating step comprises 1) mixing the at least one inhibitor with the at least one polysaccharide at a highly hydrated state thereby encapsulating the at least one inhibitor in a polysaccharide network, and 2) dehydrating the polysaccharide network thereby controlling release kinetics or final swell ratio. In another embodiment, the incorporating step comprises 1) encapsulating at least one inhibitor into a biocompatible or biodegradable vessel and 2) combining the polysaccharide and the vessel into a gel formulation. The polysaccharide gel formulations described herein can be used for a variety of cosmetic applications.

5 Claims, 4 Drawing Sheets

(56) References Cited

U.S. PATENT DOCUMENTS

| | | |
|---|---|---|
| 5,935,164 A | 8/1999 | Iversen |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,192,984 B2 | 3/2007 | Berg et al. |
| 7,196,180 B2 | 3/2007 | Aeschlimann |
| 7,314,636 B2 | 1/2008 | Caseres et al. |
| 7,491,709 B2 | 2/2009 | Carey |
| 7,741,476 B2 | 6/2010 | Lebreton |
| 8,124,120 B2 | 2/2012 | Sadozai |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0265389 A1 | 12/2004 | Yui et al. |
| 2005/0101582 A1 | 5/2005 | Lyons et al. |
| 2005/0136122 A1 | 6/2005 | Sadozi et al. |
| 2005/0142152 A1 | 6/2005 | Leschchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0271729 A1 | 12/2005 | Wang |
| 2005/0287180 A1 | 12/2005 | Chen |
| 2006/0040894 A1 | 2/2006 | Hunter et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton et al. |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0018102 A1 | 1/2009 | Moutet et al. |
| 2009/0022808 A1 | 1/2009 | Champion |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel et al. |
| 2009/0148527 A1 | 6/2009 | Robinson |
| 2009/0155314 A1 | 6/2009 | Tezel et al. |
| 2009/0155362 A1 | 6/2009 | Longin |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0316683 A1 | 12/2010 | Piron |
| 2011/0034684 A1 | 2/2011 | Yokokawa |
| 2011/0077737 A1 | 3/2011 | Stroumpoulis et al. |
| 2011/0118206 A1 | 5/2011 | Lebreton |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0224164 A1 | 9/2011 | Lebreton |
| 2011/0229574 A1 | 9/2011 | Guillen et al. |
| 2012/0034462 A1 | 2/2012 | Stroumpoulis et al. |
| 2012/0071437 A1 | 3/2012 | Stroumpoulis et al. |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2012/0295870 A1 | 11/2012 | Lebreton |
| 2013/0072453 A1 | 3/2013 | Gousse et al. |

FOREIGN PATENT DOCUMENTS

| | | |
|---|---|---|
| EP | 0416250 | 3/1991 |
| EP | 0416846 | 3/1991 |
| EP | 141792 | 4/2003 |
| EP | 1398131 | 3/2004 |
| EP | 1532991 | 5/2005 |
| EP | 1726299 | 11/2006 |
| EP | 2236523 | 10/2010 |
| FR | 2733427 | 5/2001 |
| FR | 2920000 | 2/2009 |
| FR | 2924615 | 1/2010 |
| JP | 55-153711 | 11/1980 |
| JP | 2007063177 | 3/2007 |
| WO | WO 86/00079 | 1/1986 |
| WO | WO 86/00912 | 2/1986 |
| WO | WO 92/00105 A | 1/1992 |
| WO | WO 92/20349 | 11/1992 |

| | | |
|---|---|---|
| WO | WO 94/01468 | 1/1994 |
| WO | WO 94/02517 | 2/1994 |
| WO | WO 96/33751 | 1/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 01/79342 | 10/2001 |
| WO | WO 02/05753 | 1/2002 |
| WO | WO 02/06350 | 1/2002 |
| WO | WO 02/09792 | 2/2002 |
| WO | WO 02/17713 | 3/2002 |
| WO | WO 03/007782 | 1/2003 |
| WO | WO 2004/020473 | 3/2004 |
| WO | WO 2004/022603 | 3/2004 |
| WO | WO2004/073759 | 9/2004 |
| WO | WO 2004/073759 | 9/2004 |
| WO | WO 2004/092223 | 10/2004 |
| WO | WO 2005/040224 | 5/2005 |
| WO | WO 2005/067994 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | 2007136738 | 11/2007 |
| WO | WO 2007/128923 | 11/2007 |
| WO | WO 2008/034176 A | 3/2008 |
| WO | WO 2008/068297 | 6/2008 |
| WO | WO 2008/072230 A | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 A | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |

OTHER PUBLICATIONS

Beer "Dermal fillers and combinations of fillers for facial rejuvenation." Dermatol. Clin. 27(4): 427-432 (2009).
Carlin, G., et al., "Effect of anti-inflammatory drugs on xanthine oxidase and xanthine oxidase induced depolymerization of hyaluronic acid," Agents and Actions. 16 (5):377-384 (1985).
Carruthers et al. "The science and art of dermal fillers for soft-tissue augmentation." J. Drugs Dermatol. 8(4): 335-350 (2009).
Falcone et al. "Crosslinked hyaluronic acid dermal fillers: a comparison of rheological properties." J Biomed Mater Res A. 87(1): 264-271 (2008).
Falcone et al. "Temporary polysaccharide dermal fillers: a model for persistence based on physical properties." Dermatol Surg. 35(8): 1238-1243 (2009).
Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).
Gold MH, "Use of Hyaluronic acid fillers for the treatment of the aging face." Clin. Interventions Aging 2(3): 369-376 (2007).
Goldberg "Breakthroughs in US dermal fillers for facial soft-tissue augmentation." J Cosmet Laser Ther. 11(4): 240-247 (2009).
Graefe, Hendrik, et al., "Sensitive and specific photometric determination of mannitol in human serum," Clin Chem Lab Med. 41 (8):1049-1055 (2003).
Kablik et al. "Comparative physical properties of hyaluronic acid dermal fillers." Dermatol. Surg. Suppl. 35(Suppl. 1): 302-312 (2009).
Lupo, MP., "Hyaluronic acid fillers in facial rejuvenation." Semin. Cutan. Med. Surg. 25(3): 122-126 (2006).
Orvisky, E., et al., "High-molecular-weight hyaluronan—a valuable tool in testing the antioxidative activity of amphiphilic drugs stobadine and vinpocetine," Pharm.Biomed.Anal. 16:419-424 (1997).
Prestwich, Glenn D., "Evaluating drug efficacy and toxicology in three dimensions: using synthetic extracellular matrices in drug discovery," Accounts of Chemical Research 41 (1):139-148 (2008).
Segura et al. "Crosslinked hyaluronic acid hydrogels: a strategy to functionalize and pattern." Biomaterials 26(4): 359-371 (2005).
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Tezel et al. "The science of hyaluronic acid dermal fillers." J. Cosmet. Laser Ther. 10(1): 35-42 (2008).
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Zheng et al. "In situ crosslinkable hyaluronan hydrogels for tissue engineering." Biomaterials 25(7-8): 1339-1348 (2004).
Millay et al.; "Vasoconstrictors in Facial Plastic Surgery"; Archives of Otolaryngology—Head & Neck Surgery; vol. 117; pp. 160-163; Feb. 1991.
Wahl, "European Evaluation of a New Hyaluronic Acid Filler Incorporating Lidocaine", Journal of Cosmetic Dermatology; vol. 7; pp. 298-303; 2008.
Adams; "An Analysis of Clinical Studies of the Uses of Crosslinked Hyaluronan, Hylan, in the Treatment of Osteoarthritis"; J. Rheumatol Suppl. ; vol. 39; pp. 16-18; Aug. 1993.
Allemann et al.; "Hyaluronic acid gel (Juvaderm) preparations in the treatment of facial wrinkles and folds"; Clinical Interventions in Aging; vol. 3, No. 4; pp. 629-634; 2008.
Bluel et al.; "Evaluation of Reconstituted Collagen Tape as a Model for Chemically Modified Soft Tissues", Biomat. Med. Dev. Art. Org.; vol. 9(1); pp. 37-46; 1981.
Capozzi et al., "Distant Migration of Silicone Gel From a Ruptured Breast Implant", Plastic and Reconstructive Surgery; vol. 62; pp. 302-303; 1978.
Champion et al., "Role of Target Geometry in Phagocytosis"; S. Proc. Nat. Acad. Sci.; vol. 103; No. 13; pp. 4930-4934; Mar. 28, 2006.
Chvapil, "Collagen Sponge: Theory and Practice of Medical Applications", J. Biomed Mater. Res., vol. II, pp. 721-741; 1977.
Clark et al., "The Influence of Triamcinolone Acetonide on Joint Stiffness in the Rat", J Bone Joint Surg; vol. 53-A; pp. 1409-1414; Oct. 1971.
Cohen et al., "Organization and Adhesive Properties of the Hyaluronan Pericellular Coat of Chrondrocytes and Epithelial Cells", Biophys J.; vol. 85; pp. 1996-2005; Sep. 2003.
Deland, "Intrathecal Toxicity Studies with Benzyl Alcohol", Toxicol Appl Pharmacol; vol. 25; pp. 153-156; 1973.
Eyre et al., Top Curr. Chem., vol. 247, pp. 207-229; 2005.
Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.
Grillo et al., "Thermal Reconstitution of Collagen from Solution and the Response to its Heterologous Implantation", JSR; vol. II, No. 1, pp. 69-82; Jan. 1962.
Hayashibara, "AA2G"; Sep. 23, 2007, http://web.archive.org/web/20079230720 10/http://www.hayashibara-intl.com/cosmetics/aa2g.html.

Helliwell, "Use of an Objective Measure of Articular Stiffness to Record Changes in Finger Joints After Intra-Articular Injection of Corticosteroid", An Theum Dis; vol. 56; pp. 71-73; 1997.

Hertzberger-Ten Cate et al., "Intra-Articular Steroids in Pauciarticular Juvenile Chronic Arthritis", Type I, Eur J Pediatr; vol. 150; pp. 170-172; 1991.

Hetherington, "Potential for Patient Harm From Intrathecal Administration of Preserved Solutions", Abstract only Med J; vol. 173(3); p. 141; Aug. 2000.

Hurst, "Adhesive Arachnoiditis and Vascular Blockage Caused by Detergents and Other Chemical Irritants: an Experimental Study", J Path Bact, vol. LXX, No. 70; pp. 167-177; 1955.

Jones et al., "Intra-Articular Hyaluronic Acid Compared to Intra-Articular Triamcinolone Hexacetonide in Inflammatory Knee Osteoarthritis", Osteoarthritis Cartilage, vol. 3; pp. 269-273; 1995.

Klein, "Skin Filling Collagen and Other Injectables of the Skin", Dermatologic Clinics; vol. 19, No. 3, pp. 491-588; Jul. 2001.

Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.

Laeschke, "Biocompatibility of Microparticles into Soft Tissue Fillers", Semin. Cutan. Med. Surg., vol. 23; pp. 214-217; 2004.

Mancinelli et al., "Intramuscular High-Dose Triamcinolone Acetonide in the Treatment of Severe Chronic Asthma", West J. Med; vol. 167(5); pp. 322-329; Nov. 1997.

McCarty et al., "Inflammatory Reaction After Intrasynovial Injection of Microcrystalline Adrenocorticosteroid Esters", Arthritis and Rheuymatism; vol. 7(4); pp. 359-367; 1964.

Remington's Pharmaceutical Science Mac Publishing Company, Easton, PA 16th Edition 1980; 1- page.

Rosenblatt et al., "The Effect of Collagen Fiber Size Distribution on the Release Rate of Proteins from Collagen Matrices by Diffusion", J. Controlled Rel., vol. 9; pp. 195-203; 1989.

Rosenblatt et al., "Chain Rigidity and Diffusional Release in Biopolymer Gels", Proceed. Inter. Symp. Control. Rel. Bioact. Mater.; vol. 20; pp. 264-265; 1993; Controlled Release Society, Inc.

Selvi et al, "Arthritis Induced by Corticosteroid Crystals", J. Rheumatology; vol. 34:3; 1 page; 2004.

Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.

Powell; "Stability of Lidocaine in Aqueous Solution: Effect of Temperature, pH, Buffer, and Metal Ions on Amide Hydrolysis"; Pharmaceutical Research; vol. 4, No. 1, 1987.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Lindvall et al.; "Influence of Various Compounds on the Degradation of Hyaluronic Acid by a Myeloperoxidase System"; Chemcio-Biological Interactions; vol. 90; pp. 1-12; 1994.

Weidmann; "New Hyaluronic Acid Filler for Subdermal and Long-Lasting Volume Restoration of the Face"; European Dermatology; pp. 65-68; 2009.

Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

Buck et al, "Injectable Fillers for our Facial Rejuvenation: a Review", Journal of Plastic, Reconstructive and Aesthetic Surgery, (2009), 62:11-18, XP002668828.

Park et al., "Biological Characterization of EDC-crosslinked Collagen-Hyaluronic Acid Matrix in Dermal Tissue Restoration", Biomaterials 24 (2003) 1631-1641.

Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.

Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.

Atanassoff, Peter G., et al., "The Effect of Intradermal Administration of Lidocaine and Morphine on the Response to Thermal Stimulation", Anesth Analg 1997; 84:1340-3.

Bircher, Andreas J., et al., "Delayed-type hypersensitivity to subcutaneous lidocaine with tolerance to articaine: confirmation by in vivo and in vitro tests", Contact Dermatitis 1996, 34, 387-389.

Chin, Thomas M., et al., "Allergic Hypersensitivity to Lidocaine Hydrochloride", International journal of Dermatology, vol. 19, Apr. 1980, pp. 147-148.

Desai et al., J. Pharm Sci Feb. 1995; 84 (2): 212-5.

Farley, Jon S., et al., "Diluting Lidocaine and Mepivacaine in Balanced Salt Solution Reduces the Pain of Intradermal Injection", Regional Anesthesia 19(1):48-51, 1994.

Fujinaga, Masahiko, et al., "Reproductive and Teratogenic Effects of Lidocaine in Sprague-Dawley Rats", Anesthesiology 65:626-632, 1986.

Gammaitoni, Arnold R., et al., "Pharmacokinetics and safety of continuously applied lidocaine patches 5%", Am J Health Syst Pharm, vol. 59, Nov. 15, 2002, pp. 2215-2220.

GinShiCel MH Hydroxy Propyl Methyl Cellulose, Web Page http://www.ginshicel.cn/MHPC.html, Nov. 12, 2008.

Hassan et al., Effects of Adjuvants to local anaesthetics on their duration. III. Experimental studies of hyaluronic acid. Abstract Pub Med [Acta Anesthesiol Scand. May 1985; 29(4):384-8].

Kulicke et al., "Visco-Elastic Properties of Sodium Hyaluronate Solutions," American Institue of Physics (2008).

Lamar et al., "Antifibrosis Effect of Novel Gels in Anterior Ciliary Slerotomy *ACS)," ARVO 2002 abstract.

Levy, Jaime et al., "Lidocaine hypersensitivity after subconjunctival injection", Can J Ophthalmol 2006; 41:204-6.

Mackley, et al., "Delayed-Type Hypersensitivity to Lidocaine", Arch Dermatol, vol. 139, Mar. 2003, pp. 343-346.

Matsumoto, Alan H, et al., "Reducing the Discomfort of Lidocaine Administration through pH Buffering," Journal of Vascular and Interventional Radiology, Jan.-Feb. 1994, pp. 171-175.

McCleland, Plastic Reconstructive Surg., 100(6), Nov. 1997, pp. 1466-1474.

Rehakova, Milena, et al., "Properties of collagen and hyaluronic acid composite materials and their modifications by chemical crosslinking," Journal of Biomedical Research, vol. 30, 1996, pp. 369-372 XP002590342.

Sannino et al., "Crosslinking of Cellulose Derivatives and Hyaluronic Acid with Water-Soluble Carbodiimide," Polymer 46 (2005)pp. 11206-11212.

Silver et al., "Physical Properties of Hyaluronic Acid and Hydroxypropylmethylcellulose in Solution: Evaluation of Coating Ability," Journal of Applied Biomaterials, vol. 5, 89-98 (1994).

Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.

Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.

Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.

Yun, YH et al., "Hyaluronan Microspheres for Sustained Gene Delivery and Site-Specific Targeting.", Biomaterials, vol. 25, 2004, pp. 147-157.

* cited by examiner

POLYSACCHARIDE GEL FORMULATION HAVING INCREASED LONGEVITY

CROSS REFERENCE TO RELATED APPLICATIONS

This application is a continuation of U.S. patent application Ser. No. 12/276,167, filed Nov. 21, 2008, which application claims the benefit of U.S. provisional patent application No. 60/991,473, filed Nov. 30, 2007, the entire disclosures of which applications are hereby incorporated by reference in their entireties.

FIELD OF THE INVENTION

Disclosed generally are formulations useful for increasing polysaccharide gel longevity for cosmetic or medical applications, and related methods of making and using same.

BACKGROUND

Polysaccharides are relatively complex carbohydrates. They are polymers made up of many monosaccharides joined together by glycosidic bonds. They are therefore large, often branched, macromolecules. Polysaccharides, especially hyaluronic acid (HA), have been useful in cosmetic and medical applications. These polymers have been used, for example, as fillers in soft tissue augmentation.

Residing in the extracellular space, HA functions as a space-filling, structure stabilizing, and cell protective molecule with uniquely malleable physical properties and superb biocompatibility. HA matrices are extremely viscoelastic while preserving a high level of hydration. A strong correlation exists between the water content in the skin and levels of HA in dermal tissue. As human skin ages, there are known alterations in HA content and metabolism. With these changes, there is a significant deterioration in the mechanical properties of the skin. There appears to be a relationship between youthful skin and the presence of a strong HA network in the intercellular matrix.

Unfortunately, non-cross-linked as well as cross-linked polysaccharide chains such as HA are subject to degradation through different pathways; (e.g. enzymatic, free radical) thus limiting the polymer's longevity in vivo. It is, therefore, important to develop methods and compositions that decrease the rate of natural decomposition and increase the product's persistence in vivo. There remains an unmet need for having a polysaccharide formulation which has increased longevity by being resistant to degradation.

SUMMARY

Described herein are polysaccharide gel (e.g. hyaluronic acid, HA) formulations with increased longevity, or increased degradation time, in vivo. This increase in degradation time is provided by the incorporation of molecules that act as inhibitors to degradation. Further, the present disclosure provides methods for encapsulating these formulations to sustain a prolonged longevity or degradation time in vivo. The present disclosure also relates to the preparation of gels that can have pharmaceutical or cosmetic applications.

In one embodiment described herein is a polysaccharide gel formulation comprising at least one polysaccharide selected from the group consisting of hyaluronic acid, cellulose, chitosan, o-sulfated HA, dextran, dextran sulfate, chondroitin sulfate, dermatan sulfate, keratin sulfate, heparin, heparin sulfate, and alginate, and at least one inhibitor of polysaccharide degradation selected from the group consisting of a glycosaminoglycan, an antioxidant, a flavonoid, a protein, a fatty acid, and combinations thereof. In one embodiment, the polysaccharide is cross-linked. In one embodiment, the at least one polysaccharide is hyaluronic acid.

In one embodiment, the glycosaminoglycan is selected from the group consisting of heparin, heparin sulfate, dermatan sulfate, chondroitin sulfate, o-sulfated hyaluronic acid, linamarin and amygdalin. In another embodiment, the glycosaminoglycan is chondroitin sulfate and is present at a concentration of about 1% to about 40% by weight.

In one embodiment, antioxidant is selected from the group consisting of ascorbic acid, melatonin, vitamin C, vitamin E and combinations thereof.

In one embodiment, the flavonoid is selected from the group consisting of luteolin, apigenin, tangeritin, quercetin, kaemferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannis, condensed tannis, hydrolysable tannis and combinations thereof. In another embodiment, the flavonoid is tannic acid and is present at a concentration of about 0.0001 to about 1% by weight.

In one embodiment, the protein is a serum hyaluronidase inhibitor. In another embodiment, the fatty acid is a saturated $C_{10-22}$ fatty acid.

In one embodiment, the formulation further comprises a biocompatible or biodegradable vessel wherein the inhibitor is inside or part of said vessel, wherein the vessel is a liposome, micelle, or polymerized vesicle. In another embodiment, the inhibitor provides the formulation with improved rheological properties resulting in less extrusion force required for administration of the formulation compared to a cross-linked polysaccharide gel formulation.

In one embodiment described herein is a method of producing a polysaccharide gel formulation comprising having an increased degradation time comprising the step of: providing at least one polysaccharide selected from the group consisting of hyaluronic acid, cellulose, chitosan, o-sulfated HA, dextran, dextran sulfate, chondroitin sulfate, dermatan sulfate, keratin sulfate, heparin, heparin sulfate, and alginate and incorporating in the polysaccharide at least one inhibitor of polysaccharide degradation selected from the group consisting of a glycosaminoglycan, antioxidant, flavonoid, protein and fatty acid.

In one embodiment of the method, the incorporating step comprises 1) mixing the inhibitor with the polysaccharide at a highly hydrated state thereby encapsulating the inhibitor in a polysaccharide network, and 2) dehydrating the polysaccharide network thereby controlling release kinetics or final swell ratio.

In another embodiment of the method, the at least one polysaccharide is cross-linked before incorporation of the at least one inhibitor of polysaccharide degradation using a cross-linker selected from the group consisting of 1,4-butanediol diglycidyl ether (BDDE), 1,2-bis(2,3-epoxypropoxy) ethylene, 1-(2,3-epoxypropyl)-2,3-epoxycyclohexane and combinations thereof.

In one embodiment of the method, the incorporating step comprises 1) encapsulating an inhibitor into a biocompatible or biodegradable vessel and 2) combining the at least one polysaccharide and the vessel into a gel formulation.

In one embodiment described herein is a polysaccharide gel formulation with an increased degradation time comprising cross-linked hyaluronic acid and tannic acid, wherein the tannic acid is present at a concentration of about 0.0001% to about 1%.

In one embodiment described herein is a polysaccharide gel formulation with an increased degradation time comprising cross-linked hyaluronic acid and chondroitin sulfate, wherein the chondroitin sulfate is present at a concentration of about 1% to about 40%.

Further described herein are pharmaceutical compositions comprising a polysaccharide gel formulation, a pharmaceutically acceptable carrier, and an active ingredient. In one embodiment, the active ingredient is selected from the group consisting of anti-itch, anti-cellulite, anti-scarring, anti-inflammatory agents, antioxidants, vitamins, moisturizers and combinations thereof.

DETAILED DESCRIPTION

Figure 1:
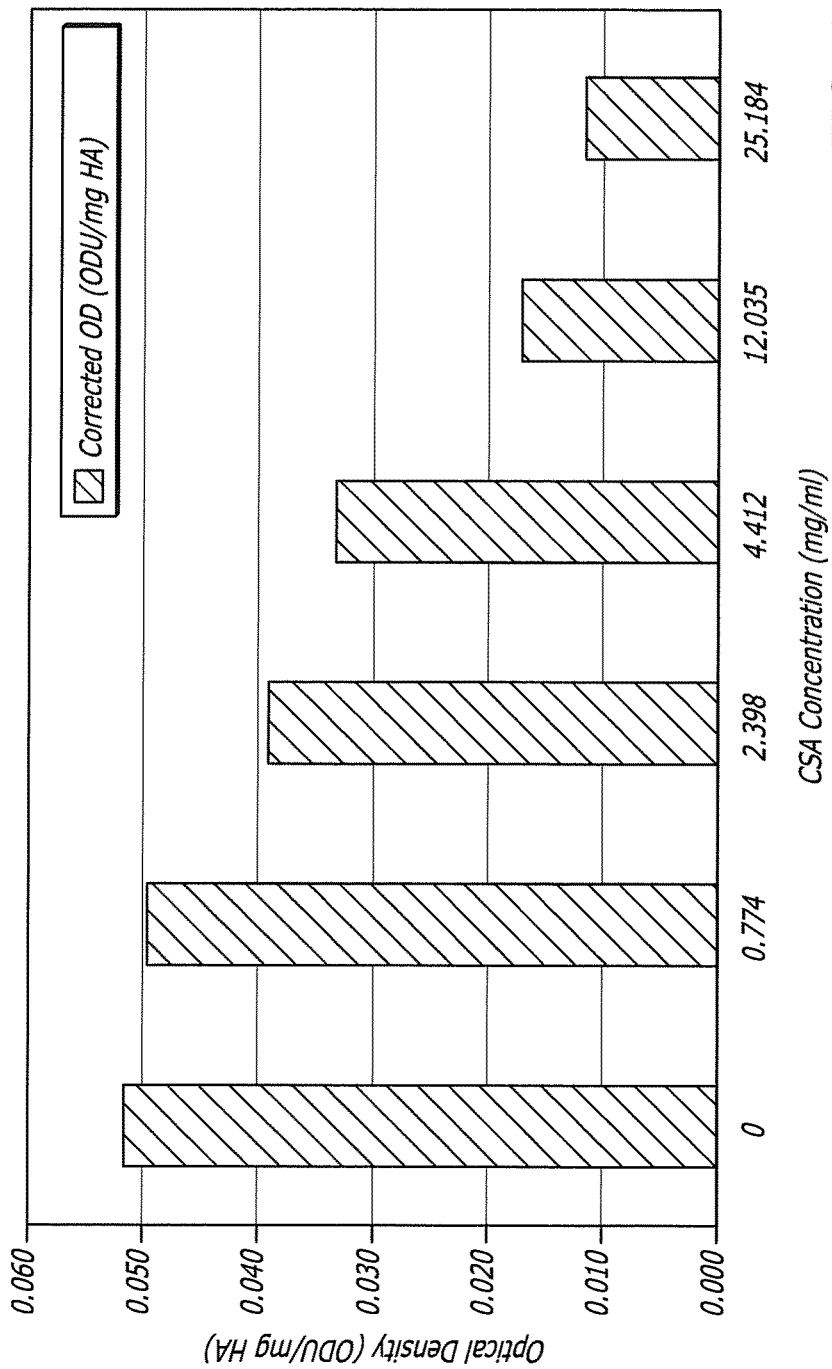
FIG. 1 graphically illustrates the extent of enzymatic degradation of polysaccharide gels including chondroitin sulfate A (CSA) using a calorimetric assay.

Described herein are polysaccharide gel (e.g. hyaluronic acid, HA) formulations with increased longevity, or increased degradation time, in vivo provided by incorporating molecules that act as inhibitors to degradation. In some embodiments, the polysaccharide gels are cross-linked. Further, the present disclosure also relates to methods for encapsulating these formulations to sustain a prolonged longevity or degradation time in vivo. The present disclosure also relates to the preparation of gels that can have pharmaceutical or cosmetic applications.

One aspect of the present disclosure relates to polysaccharide gel formulations comprising at least one polysaccharide and at least one inhibitor of polysaccharide degradation. The present disclosure further relates to increasing the degradation time of polysaccharide gels by incorporating inhibitors to degradation. "Polysaccharide" refers to a polymer of more than two monosaccharide molecules, of which the monosaccharides can be identical or different. The polysaccharide of the present disclosure can be cross-linked or not cross-linked. The polysaccharides used herein can be, but are not limited to, HA, cellulose, chitosan, o-sulfated HA, dextran, dextran sulfate, chondroitin sulfate, dermatan sulfate, keratin sulfate, heparin, heparin sulfate, and alginate.

Inhibitors are molecules that act by targeting and neutralizing specific degradation mechanisms such as enzymatic and free radical degradation. Molecules that display inhibitory activity include but are not limited to glycosaminoglycans (GAGs), (e.g. heparin, heparan sulfate, dermatan sulfate, chondroitin sulfate, o-sulfated HA, linamarin and amygdalin), antioxidants (e.g. ascorbic acid, melatonin, vitamin C and vitamin E), proteins (e.g. serum hyaluronidase inhibitor) and fatty acids (e.g. saturated $C_{10}$ to $C_{22}$ fatty acids).

Inhibitors are typically molecules orders of magnitude smaller than cross-linked polysaccharide polymers. Due to their small size and higher diffusivity, they are prone to fast adsorption in vivo that could potentially limit their performance. One method of increasing the local half-life of such molecules in vivo is to chemically graft them to the polysaccharide polymer network and deliver them simultaneously. One disadvantage of this method is that the bound molecule may display significantly lower activity compared to the unbound one. In the present polysaccharide gel formulation, the inhibitor concentration can be in the range of about 0.0001% to about 99% by wt, about 0.001% to about 75% by weight, about 0.01% to about 60% by weight, about 1% to about 50% by weight, about 1% to about 40% by weight, about 1% to about 30% by weight, about 1% to about 20% by weight, about 10% to about 20% by weight, about 20% to about 30% by weight 0.0001% to about 0.01% by weight, about 0.0001% to about 0.1% by weight, about 0.0001% to about 1% by weight, about 0.001% to about 1% by weight, about 0.01% to about 1% by weight, or about 1% to about 10% by weight.

Another aspect of the present disclosure relates to a method of producing a polysaccharide gel formulation having reduced degradation comprising providing a polysaccharide and encapsulating an inhibitor of degradation in the polysaccharide.

Non-cross-linked as well as cross-linked polysaccharide chains are subject to degradation through different pathways (e.g. enzymatic, free radical) that often limits the polymer's longevity in vivo. It is therefore important to develop ways that decrease the rate of this natural decomposition process and increase the product's persistence in tissues.

One method for achieving increased polysaccharide persistence is to encapsulate inhibitor molecules within the polysaccharide polymer network itself or into large vessels within the network that would enable local (injection site), sustained and controlled release of degradation inhibitors. This would also allow avoidance of the natural degradation mechanisms. The present encapsulation method provides a constant supply of degradation inhibitors to the polysaccharide polymer network over a period of weeks. In other embodiments, a constant supply of degradation inhibitors is provided over a period of months. One method of encapsulation is to incorporate the degradation inhibitors within the polysaccharide polymer network either by adsorption or by an encapsulation process. In the latter case, the inhibitors are allowed to mix with the polysaccharide network at a highly hydrated state, followed by dehydration of the network to control the release kinetics (e.g. final swelling ratio of the polymer). A highly hydrated state corresponds to an HA concentration that is less than about 20 mg/ml.

The final swelling ratio can be controlled by adjusting the pH or partially dehydrating the polysaccharide network. The contracted network can be sized into particles, mixed with the polysaccharide gel and delivered at the site of the injection. The slow re-hydration of the inhibitor-loaded polysaccharide particles can provide a sustained and controlled delivery of their active content.

Another aspect of the present disclosure relates to a polysaccharide gel formulation comprising a polysaccharide and an inhibitor of polysaccharide degradation, and further comprising a biocompatible or biodegradable vessel wherein the inhibitor is inside or part of the vessel. Such vessels can be composed of non-covalently or covalently linked self-assembled molecules such as liposomes, micelles, and polymerized vesicles.

A liposome is a vesicle composed of one or more bilayer membranes formed of naturally-derived phospholipids with mixed lipid chains (such as egg phosphatidylethanolamine), or of pure surfactant components like dioleoylphosphatidylethanolamine (DOPE). Liposomes, usually but not by definition, contain a core of aqueous solution; lipid structures that contain no aqueous material are called micelles. A micelle is an aggregate of surfactant molecules dispersed in a liquid colloid. A typical micelle in aqueous solution forms an aggregate with the hydrophilic "head" regions in contact with surrounding solvent, sequestering the hydrophobic "tail" regions in the micelle center. This type of micelle is known as a normal phase micelle (oil-in-water micelle). Inverse micelles have the headgroups at the centre with the tails extending out (water-in-oil micelle). Micelles are often approximately spherical in shape, however, other forms, including shapes such as ellipsoids, cylinders, and bilayers are also possible. The shape and size of a micelle is a function of the molecular geometry of its surfactant molecules and solution conditions such as surfactant concentration, temperature, pH, and ionic strength. The process of forming micelles is known as micellization and forms part of the phase behavior of many lipids according to their polymorphism.

Another aspect of the present disclosure relates to a method for producing a polysaccharide gel formulation having reduced degradation comprising the steps of 1) providing a polysaccharide, 2) incorporating an inhibitor into a biocompatible or biodegradable vessel and 3) combining said polysaccharide and vessel into a gel formulation. This method of encapsulation thus incorporates the inhibitors into biocompatible and biodegradable vessels that could be delivered at the same time with the polysaccharide. Such vessels can be composed of non-covalently or covalently linked self-assembled molecules (e.g. micelles, liposomes, and polymerized vesicles). Self-assembly is a term used herein to describe processes in which a disordered system of pre-existing components forms an organized structure or pattern as a consequence of specific, local interactions among the components themselves, without external direction.

An additional advantage of the proposed formulation is the increased tune-ability of the final product's rheological properties. Cross-linked polysaccharide gels typically have high viscosity and require considerable force to extrude through a fine needle. Uncross-linked polysaccharides are often used as lubricants to facilitate this extrusion process. However, especially in HA dermal fillers, uncross-linked HA does not contribute to the persistence of the final product in vivo. In fact, the more cross-linked HA is replaced by uncross-linked HA to tune the rheological properties of the dermal filler (for a fixed total HA concentration), the lower the degradation resistance of the product will be. Instead, according to the proposed formulation, uncross-linked GAGs that are also inhibitors to degradation (e.g. chondroitin sulfate, o-sulfated hyaluronic acid) can be used both to extend the longevity and improve the rheological properties of the final product.

The polysaccharides described herein can be cross-linked or uncross-linked. A cross-linking agent can be used to cross-link the polysaccharides according to the present description. The cross-linking agent may be any agent known to be suitable for cross-linking polysaccharides and their derivatives via their hydroxyl groups. Suitable cross-linking agents include but are not limited to, for example, 1,4-butanediol diglycidyl ether (or 1,4-bis(2,3-epoxypropoxy)butane or 1,4-bisglycidyloxybutane, all of which are commonly known as BDDE), 1,2-bis(2,3-epoxypropoxy)ethylene and 1-(2,3-epoxypropyl)-2,3-epoxycyclohexane. The use of more than one cross-linking agent or a different cross-linking agent is not excluded from the scope of the present disclosure. In one embodiment, the cross-linking agent comprises or consists of BDDE.

Dermal fillers can be used to treat moderate to severe facial wrinkles and folds such as nasolabial folds (those lines that extend from the nose to the corners of the mouth). Dermal fillers can be a gel implant that includes HA, a natural complex sugar that bolsters skin elasticity, providing a smooth and supple appearance. It is biocompatible and can supplement the body's natural HA, which aging can deplete.

A dermal gel can be injected with a syringe into the mid to deep dermis of the face. The dermis is the subsurface skin layer that contains connective tissue, nerve endings, sweat and oil glands, and blood vessels. Dermal fillers can improve the skins appearance by lifting and adding volume to the wrinkles and folds in the treatment area.

Another aspect of the present disclosure relates to a cosmetic composition comprising the present polysaccharide gel formulation, a cosmetic carrier, and an active ingredient. The cosmetic active ingredients may include but are not limited to antioxidants, vitamins, and moisturizers.

As used herein, "cosmetic" is an adjective referring to improving the appearance of a surface or covering defects. Typically, cosmetic compositions can be used to improve aesthetic rather than functional aspects of a surface. Most commonly, cosmetic compositions are formulated for application as a health and beauty treatment or for affecting personal appearance of the body, for example, keratinous surfaces such as skin, hair, nails, and the like.

As used herein, "cosmetically acceptable carrier" refers to a material which is suitable for application to keratinous surfaces or other areas of the body. Upon application, cosmetically acceptable carriers are substantially free of adverse reactions with skin and other keratinous surfaces. For example, the cosmetic carriers may take the form of fatty or non-fatty creams, milky suspensions or emulsion-in-oil or oil-in-water types, lotions, gels or jellies, colloidal or non-colloidal aqueous or oily solutions, pastes, aerosols, soluble tablets or sticks.

As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with the presently disclosed polysaccharide gel in order to provide a desired composition. Those of ordinary skill in the art will recognize a number of carriers that are well known for making specific remedial pharmaceutical and/or cosmetic compositions.

Another aspect of the present disclosure relates to a pharmaceutical composition comprising the polysaccharide gel formulation, a pharmaceutical carrier and an active ingredient. As used herein, an active ingredient includes but is not limited to a drug. A drug can generally be defined as a chemical substance used in the treatment, cure, prevention, or diagnosis of disease or used to otherwise enhance physical or mental well-being.

Examples of active ingredients which can be included in the present pharmaceutical composition are anti-itch, anti-cellulite, anti-scarring, and anti-inflammatory agents. Anti-itch agents can include methyl sulphonyl methane, sodium bicarbonate, calamine, allantoin, kaolin, peppermint, tea tree oil and combinations thereof. Anti-cellulite agents can include forskolin, xanthine compounds such as, but not limited to, caffeine, theophylline, theobromine, and aminophylline, and combinations thereof. Anti-scarring agents can include IFN-γ, fluorouracil, poly(lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine and combinations thereof.

A polysaccharide such as HA is found naturally in many tissues of the body, such as, but not limited to, skin, cartilage, and the vitreous humor. It is therefore well suited to biomedical applications targeting these tissues. HA can be used in eye surgery (i.e., corneal transplantation, cataract surgery, glaucoma surgery and surgery to repair retinal detachment). HA is also used to treat osteoarthritis of the knee. Such treatments, called visco-supplementation, are administered as a course of injections into the knee joint and are believed to supplement the viscosity of the joint fluid, thereby lubricating the joint, cushioning the joint, and producing an analgesic effect. It has also been suggested that HA has positive biochemical effects on cartilage cells. Oral use of HA has been lately suggested, although its effectiveness needs to be demonstrated. At present, there are some preliminary clinical studies that suggest that oral administration of HA has a positive effect on osteoarthritis.

Due to its high biocompatibility and its common presence in the extracellular matrix of tissues, HA can be used as a biomaterial scaffold in tissue engineering research. In some cancers, HA levels correlate well with malignancy and poor prognosis. HA is thus often used as a tumor marker for prostate and breast cancer. It may also be used to monitor the progression of the disease. HA may also be used postoperatively to induce tissue healing, notably after cataract surgery. Current models of wound healing propose that larger polymers of HA appear in the early stages of healing to physically make room for white blood cells, which mediate the immune response.

A pharmaceutical composition can optionally include one or more agents such as, without limitation, emulsifying agents, wetting agents, sweetening or flavoring agents, tonicity adjusters, preservatives, buffers antioxidants and flavonoids. Tonicity adjustors useful in a pharmaceutical composition of the present disclosure include, but are not limited to, salts such as sodium acetate, sodium chloride, potassium chloride, mannitol or glycerin and other pharmaceutically acceptable tonicity adjusters. Preservatives useful in the pharmaceutical compositions described herein include, without limitation, benzalkonium chloride, chlorobutanol, thimerosal, phenyl mercuric acetate, and phenyl mercuric nitrate. Various buffers and means for adjusting pH can be used to prepare a pharmaceutical composition, including but not limited to, acetate buffers, citrate buffers, phosphate buffers and borate buffers. Similarly, antioxidants useful in pharmaceutical compositions are well known in the art and includes for example, sodium metabisulfite, sodium thiosulfate, acetylcysteine, butylated hydroxyanisole and butylated hydroxytoluene. Flavonoids are compounds found in plants that are well known to have diverse beneficial biochemical and antioxidant effects. Subcategories of flavonoids include: flavones, flavonols, flavanonse and flavanonols. Examples of flavonoids include: luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannis, condensed tannis, and hydrolysable tannis. It is understood that these and other substances known in the art of pharmacology can be included in a pharmaceutical composition of the invention. See for example, *Remington's Pharmaceutical Sciences* Mac Publishing Company, Easton, Pa. 16$^{th}$ Edition 1980.

Some of the advantages of the invention are illustrated below using examples which describe the preparation of an HA filling gel according to the methods described herein, the preparation of an HA filling gel according to the prior art and the degradation tests performed on those samples.

Molecular weight ($M_w$) as used herein refers to the sum of the atomic weights of the atoms in a molecule. For example, that of methane ($CH_4$) is 16.043 g/mol, the atomic weights being carbon=12.011 g/mol, hydrogen=1.008 g/mol. A Dalton (Da) is a unit of mass equal to $\frac{1}{12}$ the mass of $^{12}O$ and one million Da can be notated as 1 MDa.

EXAMPLE 1

Preparation of a HA Filling Gel According to the Present Disclosure

One to five grams of polysaccharide filler with a HA concentration of 24 mg/mL, about a 6% degree of cross-linking and a G' of about 180 (JUVÉDERM® 24HV, (Allergan Inc., Irvine, Calif.)) are mixed with 1000 µl of a phosphate buffered saline (PBS) solution (pH~7) that is supplemented with 10-200 mg of chondroitin sulfate A (CSA–$M_w$=5,000-120,000 Da). The mixture is mechanically homogenized.

EXAMPLE 2

Preparation of a HA Filling Gel by the Process of the Prior Art

One to five grams of polysaccharide filler with a HA concentration of 24 mg/mL, about a 6% degree of cross-linking and a G' of about 180 (JUVÉDERM® 24HV) are mixed with 1000 µl of PBS such that the final HA concentration is the same as in Example 1. The mixture is mechanically homogenized.

EXAMPLE 3

An Alternative Preparation of a Hyaluronic Acid Filling Gel According to the Present Disclosure One to five grams of a HA based polysaccharide filler with a HA concentration of 24 mg/mL, about a 6% degree of cross-linking and a G' of about 170 (JUVÉDERM® 30) are mixed with 50 µl of PBS solution (pH~7) that is supplemented with 1-20 mg of tannic acid (TA–$M_w$=800-4,000 Da). The mixture is mechanically homogenized.

EXAMPLE 4

An Alternative Preparation of a Hyaluronic Acid Filling Gel by the Process of the Prior Art One to five grams of a HA based polysaccharide filler with a HA concentration of 24 mg/mL, about a 6% degree of cross-linking and a G' of about 170 (JUVÉDERM® 30) are mixed with 50 µl of PBS such that the final HA concentration is the same as in Example 3. The mixture is mechanically homogenized.

EXAMPLE 5

Preparation of a Hyaluronic Acid Filling Gel According to the Present Disclosure One gram of sodium hyaluronate fibers (NaHA, $M_w$=0.5-3 MDa) is mixed with 5-10 g of 1% sodium hydroxide solution and the mixture is left to hydrate for 1-5 hrs.

Fifty to two hundred milligrams of 1,4-butanediol diglycidyl ether (BDDE) are added to the NaHA gel and the mixture is mechanically homogenized.

The mixture is then placed in a 40-70° C. oven for 1-4 hrs.

The resulting cross-linked hydrogel is neutralized with an equimolar amount of hydrochloric acid (HCl) and swelled in PBS (pH=7).

Ten to two hundred milligrams of CSA ($M_w$=5,000-120,000 Da) are added and the hydrogel is mechanically homogenized.

EXAMPLE 6

Preparation of an Hyaluronic Acid (HA) Filling Gel by the Process of the Prior Art One gram of NaHA ($M_w$=0.5-3 MDa) is mixed with 5-10 g of 1% sodium hydroxide solution and the mixture is left to hydrate for 1-5 hrs.

Fifty to two hundred milligrams of BDDE (same HA:cross-linker molar ratio as in Example 5) are added to the NaHA gel and the mixture is mechanically homogenized.

The mixture is then placed in a 40-70° C. oven for 1-4 hrs.

The resulting cross-linked hydrogel is neutralized with an equimolar amount of hydrochloric acid (HCl) and swelled in PBS (pH=7) such that the final HA concentration is the same as in Example 5. The obtained hydrogel is mechanically homogenized.

EXAMPLE 7

Enzymatic Degradation Study (Colorimetric Test)

Resistance to enzymatic degradation of the HA filling gels prepared in Examples 1 and 2, was evaluated using the Morgan-Elson colorimetric assay. This assay is used to estimate the average molecular weight of the HA chains before and after enzymatic degradation.

Hyaluronidase (0.1-10 mg) was added to the HA samples for 10-250 mins at 37° C. followed by 0.1 ml of a 0.8 M potassium tetraborate solution and heating at 100° C. for 10 mins. The samples were supplemented with 3 ml of a 10% (wt) p-dimethylaminobenzaldehyde solution in acetic acid and incubated at 37° C. for 10-120 mins. The change in the optical density (OD) at 585 nm post and pre-degradation was used to quantify the extent of degradation in each sample.

The results of the measurements made on the filling gels prepared according to the methods of the present disclosure and according to the prior art shown in FIG. 1 (Enzymatic Degradation Test Results (Colorimetric Assay)) indicate that the OD values of the gel prepared by the methods of the present disclosure (Example 1: 0.774-25.184 mg/ml CSA) are lower than that of the gel prepared by the process of the prior art (Example 2: 0 mg/ml CSA). Furthermore, the decrease in the OD values is proportional to the concentration of CSA. Since the OD value represents the extent of degradation, the results suggest that the gels prepared according to the present methods display a 3-75% higher enzymatic degradation resistance than the gel prepared according to the prior art.

Figure 2:
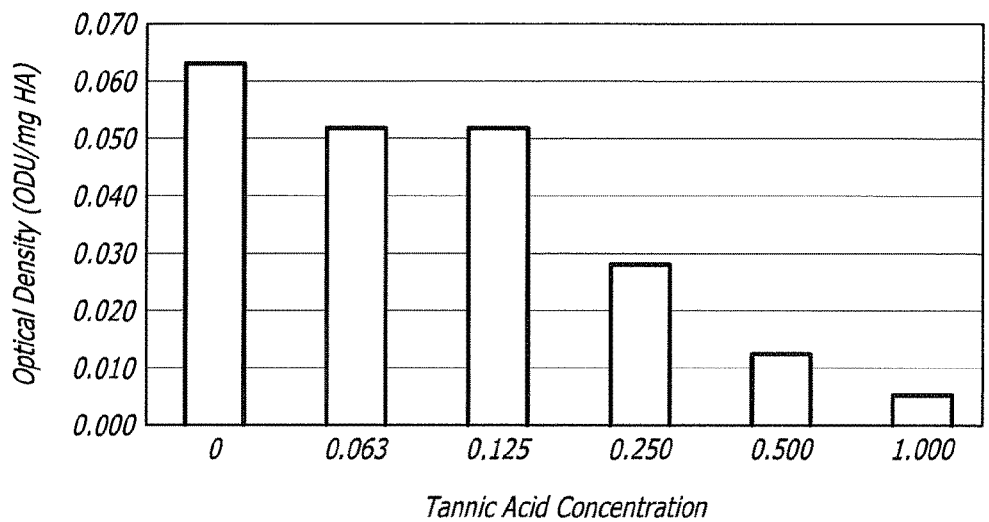
FIG. 2 graphically illustrates the extent of enzymatic degradation of polysaccharide gels including tannic acid (TA) using a colorimetric assay.

Similarly to the case of the CSA supplemented gels, the OD values of the TA supplemented gels prepared by the methods of the present disclosure, as shown in FIG. 2, (Example 3: 0.063-1.000 mg/mL TA) are lower than that of the gel prepared by the method of the prior art (Example 4: 0 mg/mL TA). Furthermore, the decrease in the OD values is proportional to the concentration of TA. Since the OD value represents the extent of degradation, the results suggest that the gels prepared according to the present description display a 15-90% higher enzymatic degradation resistance than the gel prepared according to the prior art. It can further be seen that TA has a higher inhibitory activity than CSA since it generally takes an order of magnitude less amount of TA to obtain the same inhibition as with CSA.

EXAMPLE 8

Enzymatic Degradation Study (Soluble HA Assay)

To further evaluate the enzymatic degradation resistance of the HA filling gels prepared in Examples 1 and 2, a SEC-MALS (Size Exclusion Multi-Angle Light Scattering) based soluble HA assay was used. This assay can be used to quantify degradation by evaluating the percentage of soluble HA (defined as the portion of the gel that can pass through a 0.2-1.0 μm filter) contained in each sample. The change in the amount of soluble HA, pre and post-degradation, can be used to quantify the extent of degradation in each sample.

The SEC-MALS tests were performed using an Agilent size exclusion chromatography system equipped with Wyatt light scattering and refractive index units. Hyaluronidase (0.1-10 mg) was added to the HA samples for 10-250 mins at 37° C. followed by 0.1 ml of a 0.8 M potassium tetraborate solution and heating at 100° C. for 10 mins. The samples were diluted in PBS, filtered through a 0.2-1.0 μm filter and injected into the SEC-MALS system. The soluble HA content before and after the enzymatic degradation as well as their difference are shown in FIG. 3.

Figure 3:
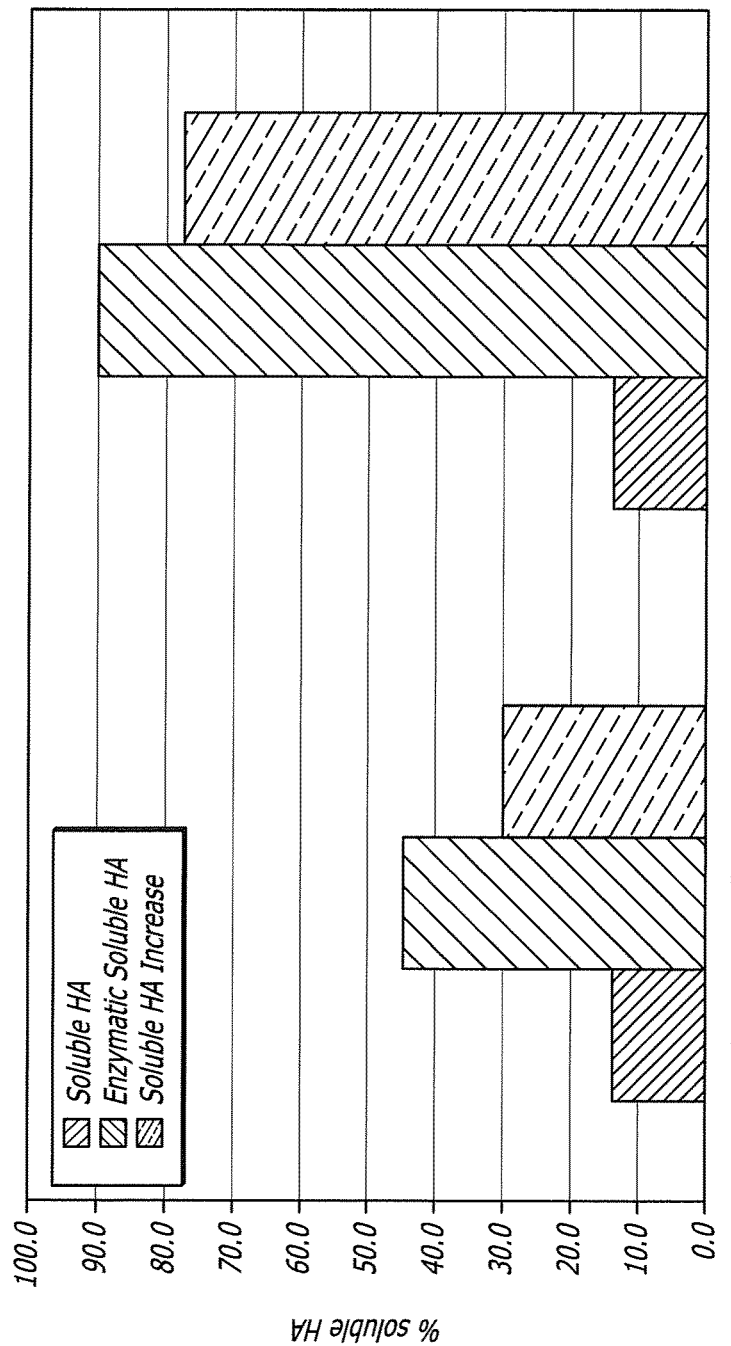
FIG. 3 graphically illustrates the extent of enzymatic degradation of polysaccharide gels both with and without CSA using a soluble HA assay.

The results shown in FIG. 3 (Enzymatic Degradation Test Results (SEC-MALS Assay)) indicate that the increase in the soluble HA content post enzymatic degradation is significantly greater for the non-CSA containing sample. This difference in the soluble HA increase between the CSA and the non-CSA samples is consistent with the results obtained in the colorimetric degradation assay and suggests that the gel prepared according to the methods of the present disclosure shows a higher degradation resistance than the gel prepared according to the prior art.

Figure 4:
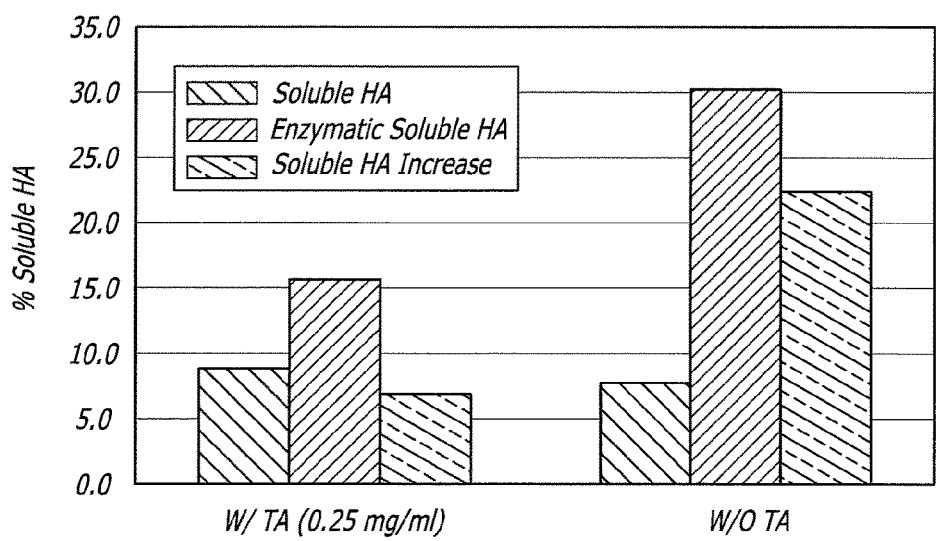
FIG. 4 graphically illustrates the extent of enzymatic degradation of polysaccharide gels both with and without TA using a soluble HA assay.

Similarly to the case of the CSA supplemented gels, the post degradation increase in the soluble HA content of the TA supplemented gels prepared by the methods of the present description (Example 3: 0.063-1.000 mg/mL TA) is lower than that of the gel prepared by the process of the prior art (Example 4: 0 mg/mL TA). These results are in agreement with the colorimetric method summarized in FIG. 4. Furthermore, it can be seen again that the inhibitory activity of TA is an order of magnitude higher than that of CSA.

EXAMPLE 9

Continuous Extrusion Force Test

To evaluate the rheological properties of the hyaluronic acid filling gels prepared in Examples 5 and 6 continuous extrusion force tests were performed on each sample. The extrusion force test can be used to determine whether CSA can facilitate the extrusion process, by acting as a lubricant.

The extrusion force tests were performed on an Instron instrument using a 5 ml syringe with a 30G needle. 0.5 ml of each sample was extruded at a constant rate of 50 mm/min. The peak force recorded quantifies the ease of extrusion. The compressive force as a function of the compressive extension for the two samples is plotted in FIG. 5.

Figure 5:
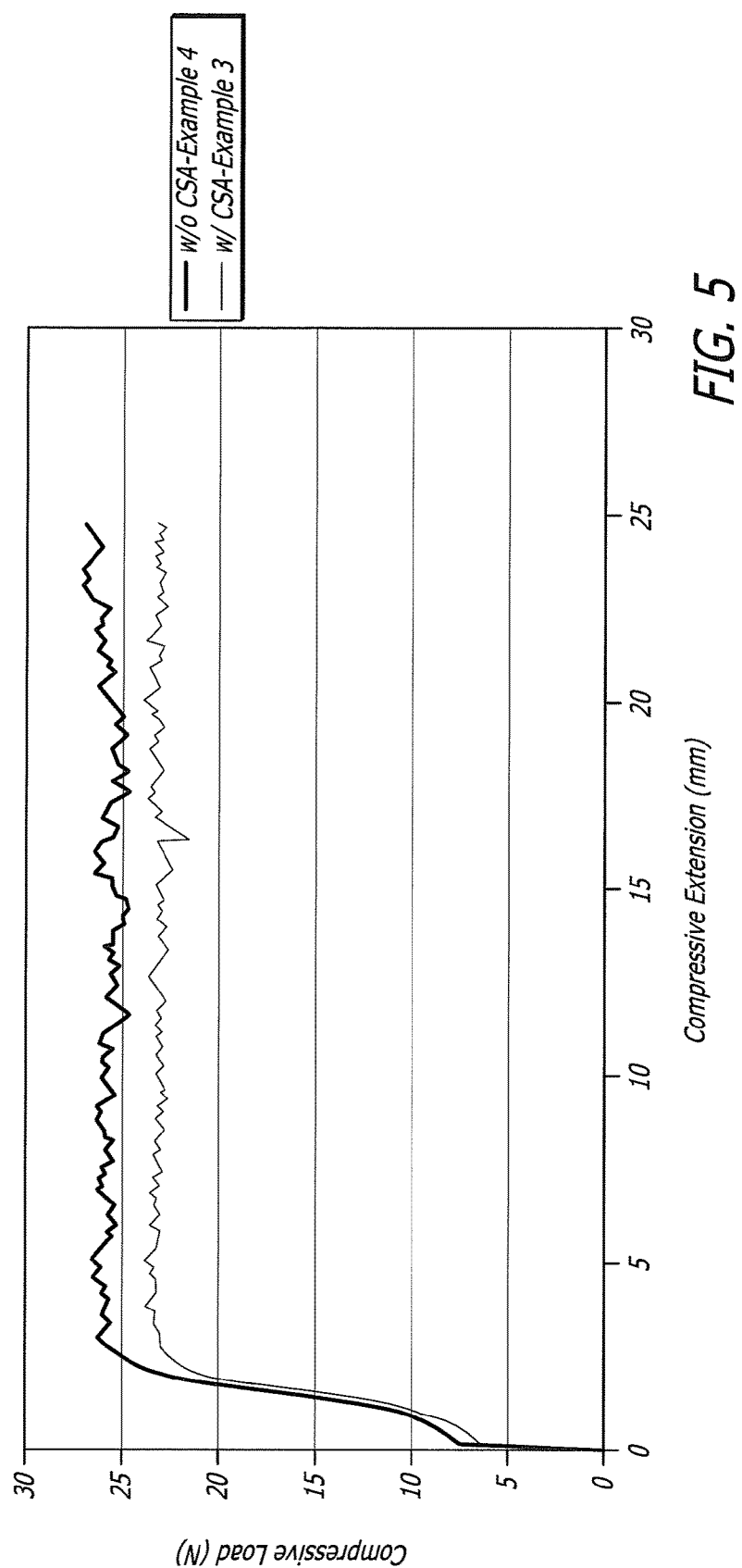
FIG. 5 graphically illustrates effects of CSA on the extrusion force of a polysaccharide gel.

The results in FIG. 5 show that the extrusion force recorded for the gel prepared by the methods described herein is lower than that of the gel prepared by the process of the prior art. This difference in the extrusion force is characteristic of the difference in gel hardness under flow and suggests that the CSA contained in the gel prepared by the methods described herein acts as a lubricant that facilitates flow.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A dermal filler formulation comprising:
   (a) at least one polysaccharide comprising crosslinked hyaluronic acid;
   (b) at least one inhibitor of polysaccharide degradation, the inhibitor comprising tannic acid present in formulation at a concentration of about 0.0001% to about 1% by weight; and
   (c) mannitol.

2. The formulation of claim 1 further comprising vitamin C.

3. The formulation of claim 1, wherein the at least one polysaccharide is in the form of a biodegradable vessel wherein said inhibitor is encapsulated in said vessel.

4. The formulation of claim 1 wherein said at least one polysaccharide further comprises a chondroitin sulfate.

5. The formulation of claim 1 wherein the at least one polysaccharide is in the form of polysaccharide polymer network and the inhibitor is incorporated into the network while the network is in a hydrated state.

* * * * *

UNITED STATES PATENT AND TRADEMARK OFFICE
CERTIFICATE OF CORRECTION

PATENT NO. : 8,513,216 B2  
APPLICATION NO. : 12/558270  
DATED : August 20, 2013  
INVENTOR(S) : Dimitrios Stroumpoulis et al.

It is certified that error appears in the above-identified patent and that said Letters Patent is hereby corrected as shown below:

On the Title Page

In item (56), under "Other Publications", in column 2, line 3, delete "Visiol" and insert -- Visual --, therefor.

In item (56), under "Other Publications", in column 2, line 16, delete "Hyroxyethyl" and insert -- Hydroxyethyl --, therefor.

On page 3, in column 2, under "Other Publications", line 59, delete "Chrondrocytes" and insert -- Chondrocytes --, therefor.

On page 3, in column 2, under "Other Publications", line 65, delete "Gonarthosis" and insert -- Gonarthrosis --, therefor.

On page 4, in column 1, under "Other Publications", line 29, delete "Rheuymatism" and insert -- Rheumatism --, therefor.

On page 4, in column 1, under "Other Publications", line 51, delete "Influcence" and insert -- Influence --, therefor.

On page 4, in column 1, under "Other Publications", line 58, delete "Crosslinekdwith" and insert -- Crosslinked with --, therefor.

On page 4, in column 1, under "Other Publications", line 58, delete "Glyol" and insert -- Glycol --, therefor.

On page 4, in column 2, under "Other Publications", line 34, delete "Institue" and insert -- Institute --, therefor.

On page 4, in column 2, under "Other Publications", line 36, delete "slerotomy" and insert -- sclerotomy --, therefor.

Signed and Sealed this
Twenty-sixth Day of May, 2015

Michelle K. Lee
*Director of the United States Patent and Trademark Office*

CERTIFICATE OF CORRECTION (continued)
U.S. Pat. No. 8,513,216 B2

In the Specification

In column 2, line 19, delete "Kaemferol" and insert -- Kaempferol --, therefor.

In column 2, line 22, delete "tannis" and insert -- tannins --, therefor.

In column 2, line 22, delete "condensed tannis" and insert -- condensed tannins --, therefor.

In column 2, line 22, delete "hydrolysable tannis" and insert -- hydrolysable tannins --, therefor.

In column 3, line 21, delete "calorimetric" and insert -- colorimetric --, therefor.

In column 7, line 65, delete "tannis" and insert -- tannins --, therefor.

In column 7, line 65, delete "condensed tannis" and insert -- condensed tannins --, therefor.

In column 7, line 65, delete "hydrolysable tannis" and insert -- hydrolysable tannins --, therefor.

In column 12, line 33, delete "consisting of or and" and insert -- consisting of and/or --, therefor.

In the Claims

In column 12, line 57, in claim 4, after "comprises" delete "a".